United States Patent
Wolfe

(10) Patent No.: US 6,332,110 B1
(45) Date of Patent: Dec. 18, 2001

(54) METHOD FOR MONITORING ADVANCED SEPARATION AND/OR ION EXCHANGE PROCESSES

(75) Inventor: Thomas D. Wolfe, Rough and Ready, CA (US)

(73) Assignee: PerLorica, Inc., Clovis, CA (US)

(*) Notice: Subject to any disclaimer, the term of this patent is extended or adjusted under 35 U.S.C. 154(b) by 0 days.

(21) Appl. No.: 09/213,781

(22) Filed: Dec. 17, 1998

(51) Int. Cl.[7] ............................ B01D 15/00; B04B 13/00
(52) U.S. Cl. ........................... 702/22; 702/30; 702/31; 702/188; 210/634; 210/638; 210/660; 210/141; 700/270; 700/271
(58) Field of Search .................. 702/22, 23, 30, 702/31, 32, 11, 12, 50, 100, 137, 188; 210/638, 642, 643, 660, 141, 142, 634; 700/270, 271, 273

(56) References Cited

U.S. PATENT DOCUMENTS 5,865,718 * 2/1999 Chan ................................. 700/273
5,993,662 * 11/1999 Garr et al. ........................ 210/256

* cited by examiner

Primary Examiner—Marc S. Hoff
Assistant Examiner—Hien Vo
(74) Attorney, Agent, or Firm—McHale & Slavin

(57) ABSTRACT

A method of monitoring advanced separation and/or ion exchange processes through the collection of localized data. The data is manipulated to generate preconfigured performance, maintenance, quality assurance, quality control, regulatory, cost reports, performance graphing and historical trends. The data is collected from sensors located at an equipment site and transferred to a remote located by use of the Internet, further all data received and used for generation of reports is also accessible by Internet connection.

29 Claims, 4 Drawing Sheets

PerLorica Web and Data Flow

PI-DATA-PLC Data Acquisition & FTP program

METHOD FOR MONITORING ADVANCED SEPARATION AND/OR ION EXCHANGE PROCESSES

FIELD OF THE INVENTION

This invention is related to the field of water treatment, and in particular, to a method of monitoring advanced separation and/or ion exchange processes by use of the world wide web allowing review of data collected and complied asynchronously from a web server.

BACKGROUND OF THE INVENTION

It is well recognized that nearly every aspect of manufacturing, as well as life itself, is dependant upon water. Water includes an infinite combination of cations and anions, metals, turbidity, dissolved solids, and so forth, all of which combine to form unique water chemistries. Technology provides the ability to adjust, reduce, or remove such constitutes which can effectively prepare water for use in a particular application. Proper water treatment provides an economically way of conditioning water to a predetermined quality level as required for the particular application.

For instance, municipal water may be obtained from any source, including seawater, all of which can be made potable by use of proper water treatment equipment. A reverse osmosis system, with minimal pretreatment, is capable of lowering the total dissolved solids of sea water into drinking water. Despite the sophistication of pretreatment, improper monitoring can allow seawater to quickly foul membranes. However, if the fouling is monitored properly, the membranes can be easily cleaned and the system will continue to run a design specifications. If the fouling is not detected quickly through proper monitoring, the membranes can be irreparably damaged requiring partial or total membrane replacement. The cost of unplanned membrane replacement, not including the revenues typically associated with down time, can make such a system cost prohibitive.

As yet another example, water is also required for steam generation in nuclear reactors. The boilers operate at a super heat which requires a very high quality of water, such as that produced by ion exchange. In this situation, it is critical that the process system is monitored properly to avoid expensive boiler cleanings and the associated down time. Such systems may also include the need to monitor hazardous boiler chemicals, such as hydrazine, requiring highly qualified personnel.

Yet another example of a manufacturer requiring very advanced separation and/or ion exchange processes are the manufacturers of microprocessors. This type of manufacturing requires an ultra-pure water quality. Again it is most critical that the water treatment process system is monitored properly to avoid latent defects in the microprocessors.

Thus, no matter what water is used for, if it requires advanced separation and/or ion exchange processes to obtain the quality required, proper monitoring of the equipment is absolutely critical. It is well recognized that the better the monitoring, the water treatment system will operate economically and reliably.

One of the problems with maintaining advanced processing equipment is a need for highly qualified individuals. Employment of a full time staff is costly and can be problematic since such monitoring is repetitively and highly qualified individuals can easily become bored. For this reason, all advanced separation processes include a large assortment of strategically placed sensors that are typically incorporated into a computer system capable of comparing the sensor values against a pre-set quality level. However, if the operator does not recognize a particular alarm condition, the elaborate array of monitoring equipment is useless.

In an effort to lessen this well recognized problems, systems have been developed for use in transferring information to a remote site for back-up monitoring of the employee's duties. However, a simple remote monitor maintains the requirement that the individual monitoring the equipment is capable of determining, what he believes, is a controllable situation. This exposes a company to the expertise of a particular employee and unless the equipment owner has a secondary source to verify operation of the equipment, loss product, loss profit, and down time will still occur.

Thus, what is lacking in the art, is a means for monitoring advanced separation and/or ion exchange processes in a cost effective manner by highly trained personnel providing the consumer with a real time analysis and economic progression of their particular equipment that can be viewed and verified at any time and from any location having access to the Internet.

SUMMARY OF THE INVENTION

The instant invention is a method of monitoring advanced separation and/or ion exchange processes through the collection of data which is manipulated to generate preconfigured performance, maintenance, quality assurance, quality control, regulatory, cost reports, performance graphing and historical trends. The data is collected from sensors located at an equipment site and transferred to a remote located by use of the Internet where all data received can be used for the generation of reports also accessible by Internet connection.

The reports, graphs and information are viewed online or downloaded by use of a web browser. The method allows a single location to monitor countless customers with each customer capable of reviewing information relevant to their equipment, all information is kept confidential by use of appropriate account names, protocols and passwords.

Thus, an objective of the instant invention is to provide a method of compiling information from a plurality of sensors mounted to advanced separation and/or ion exchange processing equipment to generate plant process, operating and economic information accessible in near real time, from any location having access to the Internet.

Another objective of the instant invention is to provide a system that operates independent of all system controls wherein no feedback is possible to the programmable logic controller or control system and to transfer such information by a local Internet provider to a consolidating Internet address.

Yet another objective of the instant invention is to provide an Internet monitoring system that can be viewed online or offline providing alarms by the use of current and historical records, providing scheduled and predicted maintenance requirements by the use of the current and historical records; providing emergency notification of failures, shutdowns, critical parameters, membrane damage by the use of electronic mail, pager, and/or human voice calling. The data is acquired from either a data capture module or by use of an improved PLC interface. Sensors are arranged to provide logical functional groupings for review and analysis (e.g. pretreatment, RO/MF train #1, /MF train #2, post treatment, ion exchange and so forth. Specific water treatment configurations include the normalization, calculations applicable to the monitoring and performance and analysis of membrane systems.

Another objective of the instant invention is to provide a method of monitoring advanced separation and/or ion exchange processes in a relatively moderate cost to the consumer while providing information that is accurate, dependable, and near real-time by use of relatively simply architecture.

Another objective of the instant invention is to provide a method of monitoring advanced separation and/or ion exchange processes which is independent and/or complimentary of the existing monitoring system.

The further objective of this invention is to provide a widely understood user interface between the underlying data generated by a process system such as the production of ultra pure water for semiconductor manufacturing and the corporate managers ultimately responsible for the entire facility's operation. Although many commercially available systems make data available from process systems over the Internet, heretofore these systems have been difficult to learn to manipulate in a facile manner. The present invention overcomes these limitations by presenting data in the context of the by now familiar web browser such as Netscape Navigator or Internet Explorer. This data is furthermore already analyzed and formatted in a configuration that allows even non-technical personnel to readily grasp the current state of system performance.

It is readily apparent that this same approach could easily be applied to other water using or water processing applications. For example, municipal water treatment and sewage treatment plants are ultimately the responsibility of elected officials. Yet these officials rarely have the technical training or time to allow them directly access the performance parameters of the systems for which they are responsible. The present invention could easily be used to provide a readily understandable presentation of the current performance of municipal water treatment system which was fully accessible by the elected officials at any time via the Internet. In addition, in this application of the technology, the same presentation of the system performance could be made accessible to the public at large, allowing interested members of the public to monitor the operation of their own drinking water plants as desired.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 1:
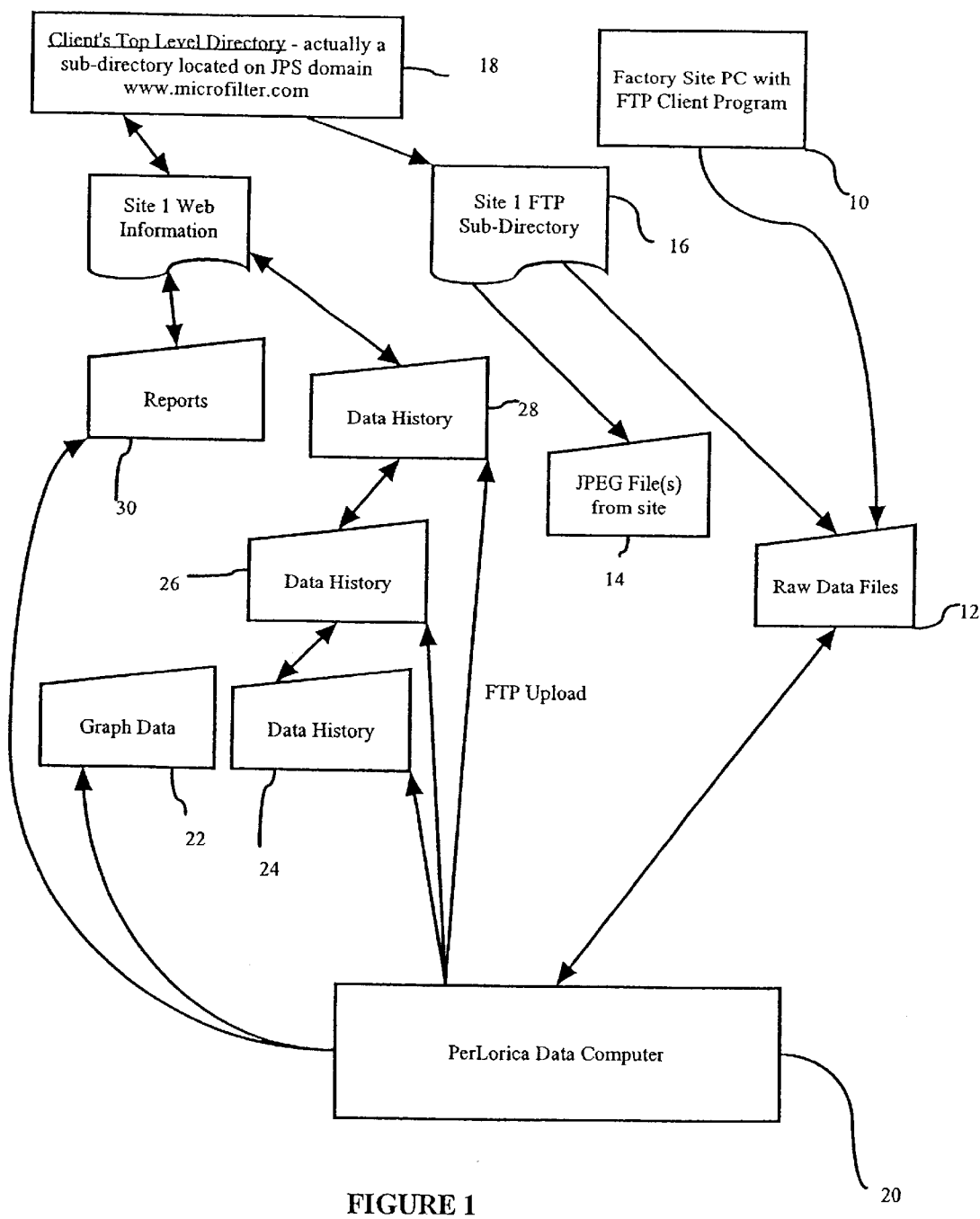
FIG. 1 is a pictorial representation of the various modules that make up the instant invention.

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

The instant invention is a monitoring system that incorporates the use of the Internet for providing a remote location for assimilation and dissemination of configured reports regarding advanced separation and/or ion exchange processes. Data is first collected by the use of sensors and on-line analytical devices from numerous locations on a water treatment system. For instance, a typical micro filter or reverse osmosis sensor group would include, but is not limited to: raw water temperature, conductivity, PH, pressure, and turbidity; permeate flow, turbidity, pressure, and conductivity; concentrate flow and pressure as well as on/off operation of the operating pump. The data generated by the sensors and on-line liquid devices are forwarded to a data capture module or programmable controller 10 which performs the required analog to digital conversion for use in transmitting data files 12 and 14 to a main server located off-site by use of local Internet access. Date files may also be transferred by modem to a processing site. The local data capture module, or programmable controller 10, continuously scans sensor data inputs and automatically logs and archives operating data at specified intervals. System operation for real time monitoring 16 by accessing an Internet web site 18 specifically set up for a particular customer. The data is also manipulated by the data computer 20 with ftp uploads wherein operating parameters are displayed graphically in a tabular format which are color coded to provide an indication of normal operation, warning status or alarm conditions. The information from the sensors are used for determining critical information for the proper evaluation of reverse osmosis membrane performance per (salt rejection, permeate flow; feed/brine average rejection and simple rejection) which is normalized in accordance with AST Standards and graphically displayed for performance evaluation, preventative maintenance, scheduling, or for trouble shooting.

Historical performance data 24 can be plotted and presented also in geographical 26 or tabular form 28 for selected periods. This provides for not only an historical analysis of system performance, but also a record of prior performance where quality control or regulatory recording purposes. In this manner, the software is designed to continuously scan sensor input and compare the current value with alarm set points in a pre-determined report 30. These set points may be different than actual locally set alarm points. For example, management may wish to see all instances where alarms were close to an alarm or trigger point and such conditions may be summarized in exception reports. The device further has the ability to notify authorized users by E-mail or use of a pager when process conditions meet or exceed, or appear likely to exceed, normal alarm conditions. This provides a layer of redundancy in system operation, and allows non technical and management personnel to be notified promptly in the event of non standard operations.

The customer is capable of accessing data related to his processing equipment including all data, information and reports by use of any computer having Internet access capability. This eliminates the need for specialized equipment and allows a manager operating at his desk to access the data from any location whether it be the office, home, or on the road without the use of specialized computer systems. The software program continually updates the reports for the customer or a customer may view the reports or download them from the web site.

In the preferred embodiment, the reports are configured to each customer's requirements when a service agreement is established, the reports are typically generated for three primary management levels: A) Process systems operations, B) Plant QA/QC and C) financial oversight. For instance, the process system operations would contain the information necessary to monitor, maintain, supervise and trouble shoot process plant system performance. In this manner the typical information and parameters process block would include, if applicable, flow rates, pressures, delta pressures, permeate and/or ion exchange quality, ph, alarm conditions, tank levels, and a graphical presentation of applicable process performance parameters and trends. A Plant QA/QC report would contain the information necessary to enable plant managers to effectively manage downstream manufacturing or distribution processes. In addition, quality assurance personnel would be able to monitor the quality and quantity of the treated water to confirm compliance with specifications and standards. Information in this report would typically include treated water production rate (flow), treated water consumption rate (flow), treated water storage volume, reserve capacity (at current production and consumption rates), final treated water quality, reports and archive data for regulatory compliance and/or QA/QC documentation.

Financial oversight would be through a plant economic report which would contain information needed by managers with profit and loss or budget responsibility to effectively track the cost of operation and to identify budget variances, when they occur, to permit timely corrective action. In this manner, typical information parameters contained in a plant economic report would include calculated power consumption (expressed in kWh and actual cost in local currency) and computed on the basis of user's supply pump/motor efficiencies both as a year to date, as a percent of the prior period, and variances both actual and budget/actual versus prior period. The parameter would also include calculated chemical consumption (expressed in volume consumption and as converted to local currency) and computed based on the user's supplied chemical dose rates and integrated feed water flow rates. This would be performed as a year to date, as a percent of the prior period, as variances both actual versus budget/actual versus prior period.

Calculated raw water consumption based on integrated water use from feed water flow rates calculated on the year to date, as a percent of the prior period, and as variances-actual versus budget/actual versus prior period.

Projected membrane element life to be provided estimated upon the operational life remaining (based on current performance and trends) and estimated sinking fund value for membrane replacement.

Calculated/estimated overall plant efficiency may be provided as a percent of theoretical efficiency. Efficiency could be based on the theoretical minimum water, power, and chemical consumption versus actual consumption calculated.

Figure 2:
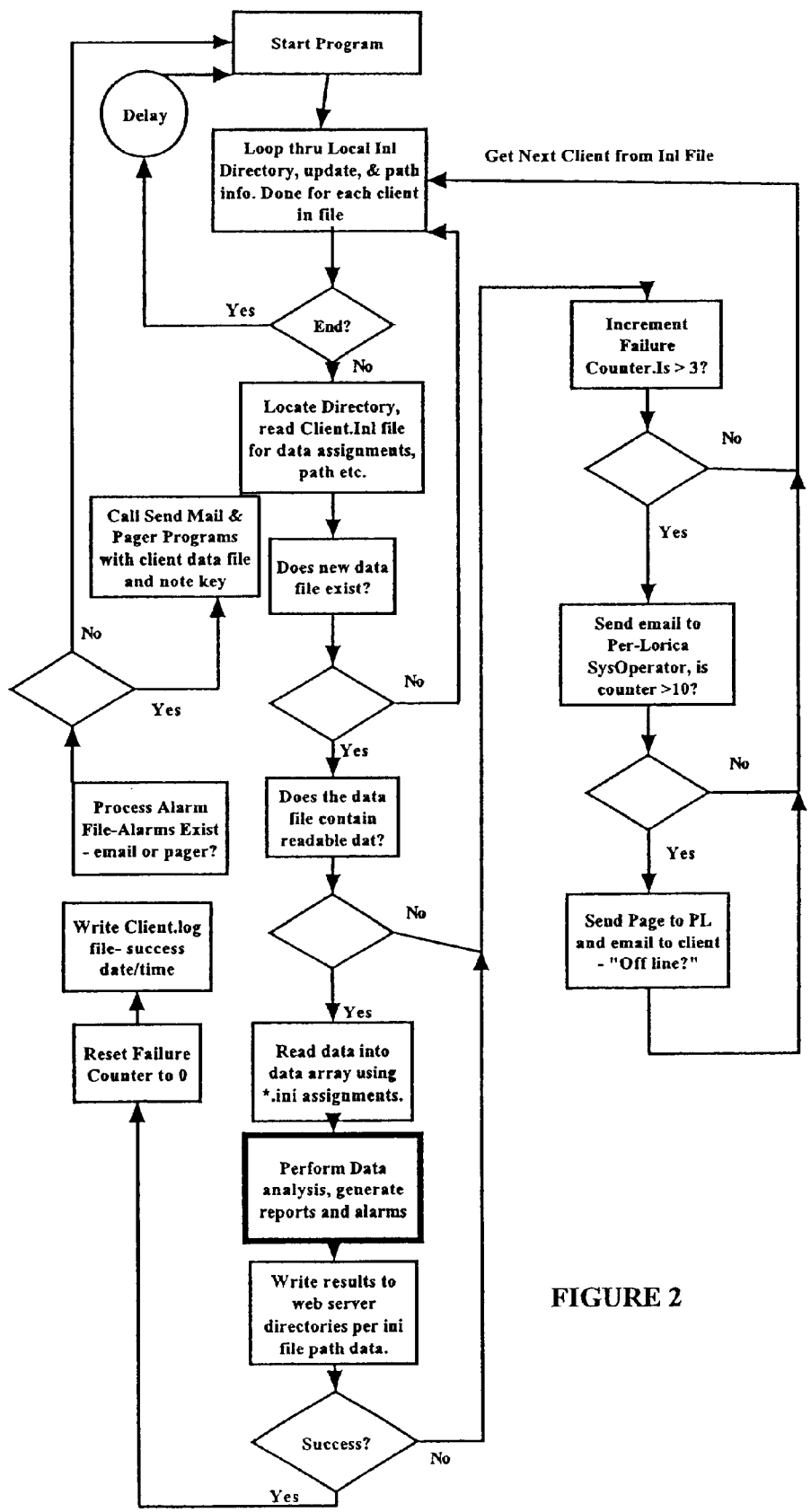
FIG. 2 is a flow diagram of the start-up operations of the software.
Figure 3:
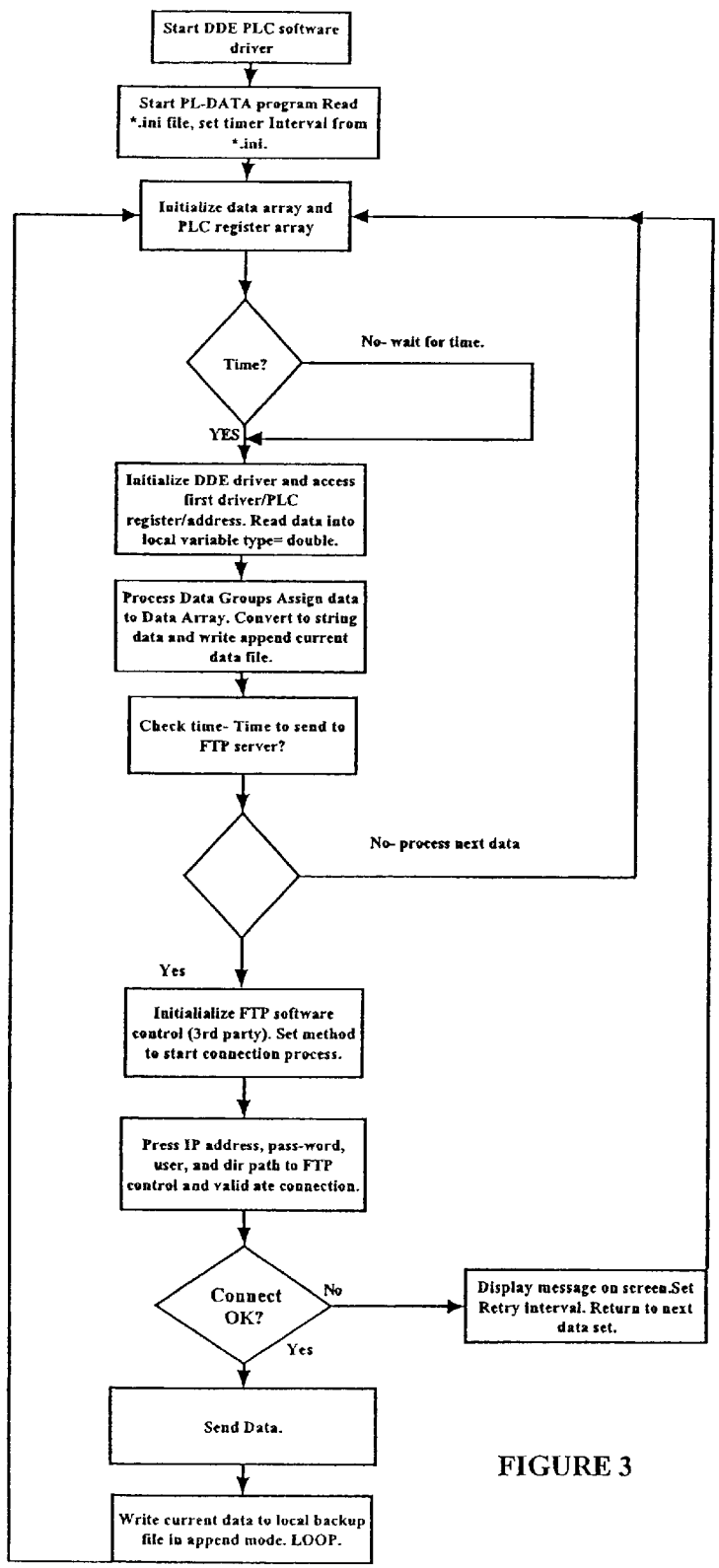
FIG. 3 is a flow diagram of the data acquisition operations of the software.
Figure 4:
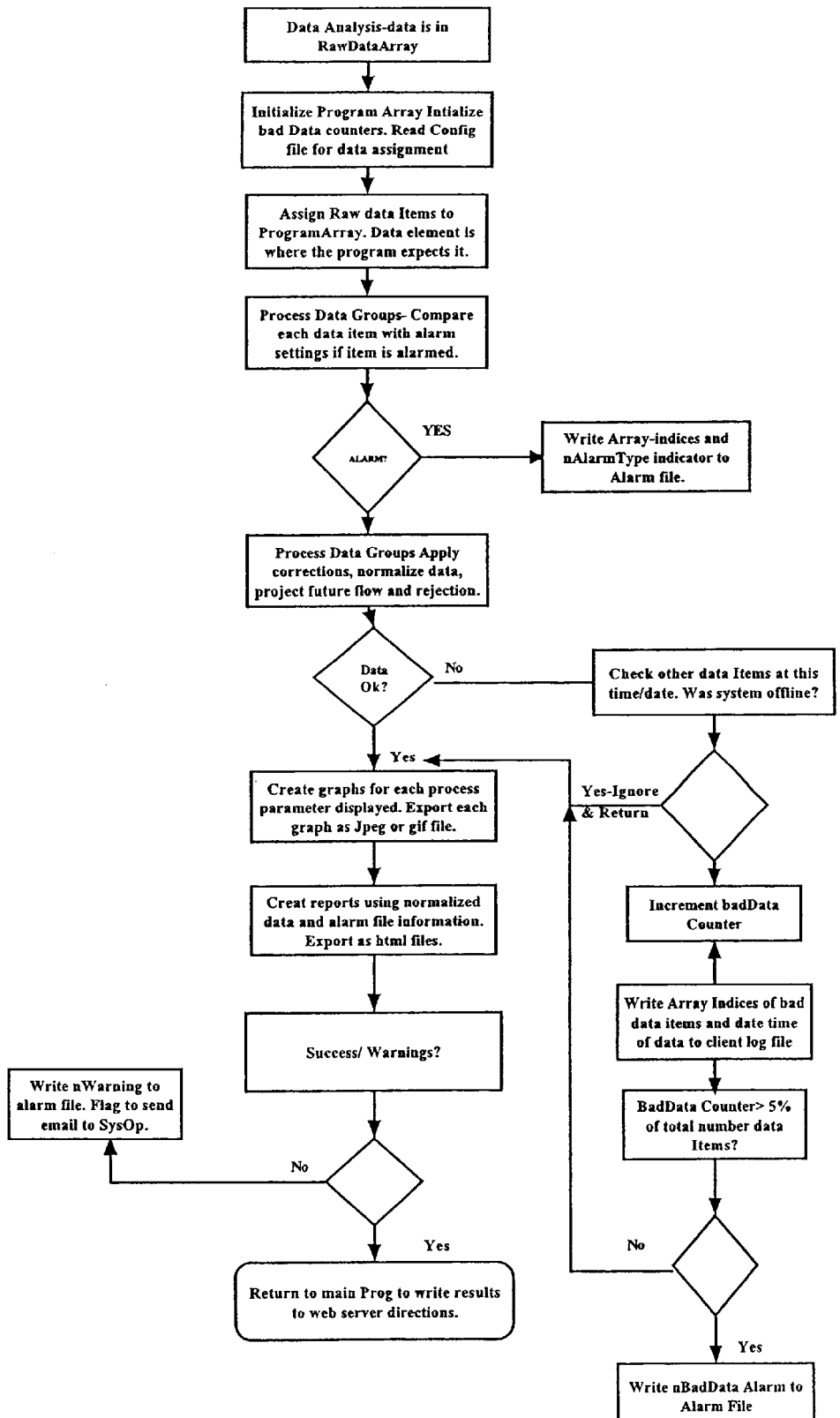
FIG. 4 is a flow diagram of the data analysis and report generator of the software.

Now referring to FIGS. 2–4, set forth is the operation of the program. This program has four essential parts—the local data capture means, the data sending means, the data computation and analysis, and the web server.

At the local site, where the process equipment is located, a serial interface board is used with a local computer to capture data from the process instruments through the serial output of the Programmable Logic Controller (PLC). A software drive specifically designed for the process PLC is utilized for this application. These drivers are available commercially and with the correct driver and some slight modification nearly every commercial PLC can be accessed. This local computer is connected to the Internet either via dial up access or through a dedicated corporate network.

A local configuration file on the local computer tells the program which PLC register addresses to access, any scaling factor which needs to be applied, a physical description of the data being collected for example—temperature or pressure, and how often the access is required. The data set collected is then converted to a comma delimited string value and stored locally on the hard disk in a sequential file. This file may also be encrypted by software if necessary.

At set intervals, usually in the order of 1–30 minutes, the local program calls a third party control software module (the data sending module) which activates the Internet connection software. Either a third party Internet Service Provider is accessed via dial up connection and a modem or a local network is used. The contents of the local data file are then sent via ftp protocol or E-mail (smtp) to either an ftp server which can be accessed by the main data computer or directly to the main data computer. The local computer uses the ftp access path and passwords stored on its hard disk in the configuration file to determine where to send the data. If the configuration file has changed since the last update, this file is also sent.

The local computer program then transfers the contents of the data file to a historical data file on the hard disk providing an on site data backup source. The current data file is then reused for storing new data. Typically the amount of data transferred each cycle to the ftp server is relatively small—several kilobytes—so that the load on the network is minimal. It will also be apparent to anyone skilled in the art of programming that this local computer, if so desired, could also be used to access the Internet and the results of main data computation could be displayed locally.

Main Computer

At the main data computer, the high level program also utilizes a series of configuration of "*.ini" files to establish the path to where the raw data exists. This data is the data which needs to be analyzed, formatted and presented. The configuration file also contains the output path names to the various directories used by each client when they access their data via a web browser.

The main program loops through each data set in turn, restarting as needed. Data is either accessed from the main computer's hard disk or downloaded from the ftp server. The configuration file allows the main program to determine which data point is which part of a typical reverse osmosis or ion exchange system. The configuration file also holds information on which units the local process collects data. For example, the configuration file may indicate that at site B, the third data item in each data set is the applied feed pressure expressed in kilopascals. The program must operate in a consistent set of units and thus translates all pressure values into the common format of pounds per square inch (psi) using a units conversion sub-program. Furthermore, in this example, the feed pressure is critical in determining the future and current performance of the system in reference to its performance when new. Furthermore, for reverse osmosis membranes, changes in pressure are related to age, production rate, and temperature and vice versa. Thus a change in flow rate may or may not indicate that the overall system's performance has changed when normalized and compared to its performance when new or recently cleaned. Prior to this invention, the complex mathematics for these conversions required some manual intervention on the part of the operator to compute the normalized conditions. The instant invention does this automatically and reports normalized data to the output.

Of course, many more process parameters are monitored, normalized, and analyzed by the computer software of this invention.

The results of these analyses are then utilized in the following manner:

Raw performance data compared to normalized or corrected data is plotted in simple, easy to understand graphs which are published in the jpeg of gif format readily usable by a web browser.

The performance is compared to predicted normal performance and if the differential exceeds predicted limits (found in the configuration files) selected individuals are automatically sent E-mail or in more extreme cases a pager or fax (paper) alert.

Process and Economic reports are prepared from the data and published as html tables for access by a web browser.

Historical data is regularly updated and new graphs are prepared, in the jpeg or gif format as noted.

Scheduled maintenance requirements are reviewed by the software and if needed within a preset time—usually within one week, or E-mail notification is sent to the designated individual.

In either case, the output is sent to the designated web directories on a web server attached to the Internet. These directories are appropriately protected for access only by authorized individuals. It may be appreciated that the physical location of the Main Data Computer, the ftp server, and the web server may be at the same location or remote from each other. In addition mirror sites can be maintained as necessary to provide reliable service.

The main computer may be either a stand alone unit or can serve as the Internet web server in itself in addition to performing the actual computations. No particular operating system is preferred for the web server and either Windows NT or UNIX may be utilized depending on convenience, reliability, and cost issues.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A method for remote monitoring and assessing the performance of advanced separation processes employing an electronic control system for monitoring selected parameters comprising the steps of:
   a) accessing raw operating data from said electronic control system;
   b) providing a storage means on a local computer for holding said raw operating data in an electronic format;
   c) coupling said local computer to an Internet server computer;
   d) transmitting said stored raw data via the world wide web using transmission methods to a remotely located Internet server computer;
   e) storing said raw data on said Internet server computer;
   f) manipulating said raw data into an analysis result; and
   g) uploading the results of said analysis result to an Internet server in a format suitable for access and visualization with a web browser program.

2. The method of claim 1 wherein said step of manipulating said raw data utilizes normalization and prediction routines to analyze the performance of a reverse osmosis membrane system.

3. The method of claim 1 wherein said step of manipulating said raw data utilizes normalization and prediction routines specifically to analyze the performance of ion exchange systems.

4. The method of claim 1 wherein said step of manipulating said raw data includes routines to analyze the results of normalization and prediction routines to notify selected individuals on the basis of the stored parameters relating to the performance of the system being analyzed.

5. The method of claim 1 wherein said step of accessing the raw data includes the steps of reading, querying, and storing data accessed from said electronic control system by use of a serial interface card.

6. The method of claim 5 wherein said step of accessing said data is integrated into said electronic control.

7. The method of claim 1 wherein said advanced separation and/or ion exchange process is defined as filtration, reverse osmosis, and deionization systems.

8. The method of claim 1 wherein said advanced separation and/or ion exchange process is defined as wastewater treatment system including secondary and/or tertiary treatment.

9. The method of claim 1 said electronic control system is defined as a programmable logic controller (PLC).

10. The method of claim 1 wherein said step of accessing raw operating data from said electronic control system includes a serial interface card coupled to said local computer, whereby said serial interface card is operable to transfer serial output of raw data from said electronic control system to the local computer.

11. The method of claim 10 wherein said local computer includes software operable to perform the stops of reading, querying, and storing data accessed from said electronic control system.

12. The method of claim 1 wherein said digital data files are transmitted to said Internet server via file transfer protocol (.ftp).

13. The method of claim 1 wherein said digital data files are transmitted to said Internet server via email.

14. The method of claim 1 including the steps of: comparing said analysis result with known optimum performance parameters, determining the differential between said known optimum performance parameters and the analysis result, and sending notifications to pre-determined recipients if known limits for differentials are exceeded.

15. A method of monitoring and assessing the performance of advanced separation processes in a water treatment having system a plurality of sensors to continuously monitor selected parameters from a remote location via the Internet, comprising the steps of:

accessing a local data collection module used capture raw data from the sensors;

providing a local storage means on a local computer for storing the collected local raw data in digital data files;

coupling said local computer to an Internet server computer;

transmitting said data files to said Internet server computer;

storing said digital data files in the memory of said Internet server computer;

accessing said digital data files from a remote coupled computer;

providing a software program on said Internet server computer operational to monitor and assess the performance of the water treatment system by analyzing the digital data to produce an analysis result; and providing the analysis result on said Internet server in a format suitable for access and visualization from a remote computer via a web browser.

16. The method of monitoring advanced separation processes in a water treatment system according to claim 15, wherein said water treatment system includes an ion exchange process.

17. The method of monitoring advanced separation processes in a water treatment system according to claim 15, wherein said software program utilizes mathematical normalization and prediction routines to produce the analysis result.

18. The method of monitoring advanced separation processes in a water treatment system according to claim 15, wherein said advanced separation processes in a water treatment system includes equipment operable to perform filtration, reverse osmosis and deionization.

19. The method of monitoring advanced separation processes in a water treatment system according to claim 15, wherein said software program is operable to monitor and assess the performance of a reverse osmosis membrane.

20. The method of monitoring advanced separation processes in a water treatment system according to claim 15, wherein said local data collection module includes a programmable logic controller (PLC) coupled to said sensors.

21. The method of monitoring advanced separation processes in a water treatment system according to claim 15 wherein said step of accessing a local data collection module further includes providing a serial interface card coupled to said local computer and said PLC, wherein said serial interface card is operable to transfer a serial output of raw data from the PLC to the local computer.

22. The method of monitoring advanced separation processes in a water treatment system according to claim 15, wherein said local computer includes software operable to perform the stops of reading, querying, and storing data accessed from the PLC.

23. The method of monitoring advanced separation processes in a water treatment system according to claim 15, wherein said digital data files are transmitted to said Internet server using secure communication means.

24. The method of monitoring advanced separation processes in a water treatment system according to claim 15, wherein said digital data files are transmitted to said Internet server via file transfer protocol (.ftp).

25. The method of monitoring advanced separation processes in a water treatment system according to claim 15, wherein said digital data files are transmitted to said Internet server via email.

26. The method of monitoring advanced separation processes in a water treatment system according to claim 15, wherein said software program is further operable perform the steps of: comparing said analysis result with known optimum performance parameters, determining the differential between said known optimum performance parameters and the analysis result, and sending notifications to pre-determined recipients if known limits for differentials are exceeded.

27. The method of monitoring advanced separation processes in a water treatment system according to claim 15, wherein said notifications are sent via email.

28. The method of monitoring advanced separation processes in a water treatment system according to claim 15, wherein said software program is operable to analyze the performance of reverse osmosis membranes.

29. The method of monitoring advanced separation processes in a water treatment system according to claim 15, wherein said software program is operable to monitor and assess the performance of ion exchange systems.

* * * * *